United States Patent
Henley (10) Patent No.: US 10,786,614 B2
(45) Date of Patent: Sep. 29, 2020

(54) ANTIGENIC DECOY ENTRAPMENT FILTRATION DEVICE AND TREATMENT METHODS FOR AUTOIMMUNE DISORDERS

(71) Applicant: Henley Development Corp., Fort Collins, CO (US)

(72) Inventor: Julian Henley, Fort Collins, CO (US)

(73) Assignee: HENLEY DEVELOPMENT CORPORATION, Fort Collins, CO (US)

( * ) Notice: Subject to any disclaimer, the term of this patent is extended or adjusted under 35 U.S.C. 154(b) by 174 days.

(21) Appl. No.: 15/790,125

(22) Filed: Oct. 23, 2017

(65) Prior Publication Data

US 2018/0110912 A1  Apr. 26, 2018

Related U.S. Application Data

(60) Provisional application No. 62/411,732, filed on Oct. 24, 2016.

(51) Int. Cl.

| | |
|---|---|
| *A61M 1/34* | (2006.01) |
| *A61M 1/36* | (2006.01) |
| *A61M 1/02* | (2006.01) |
| *B01D 63/02* | (2006.01) |
| *B01D 63/16* | (2006.01) |

(Continued)

(52) U.S. Cl.
CPC ............ *A61M 1/34* (2013.01); *A61M 1/0281* (2013.01); *A61M 1/3472* (2013.01); *A61M 1/3475* (2014.02); *A61M 1/362* (2014.02); *A61M 1/3679* (2013.01); *A61M 1/38* (2013.01); *B01D 61/28* (2013.01); *B01D 63/02* (2013.01); *B01D 63/16* (2013.01); *A61M 2202/09* (2013.01); *A61M 2205/3334* (2013.01); *B01D 61/243* (2013.01); *B01D 2315/04* (2013.01)

(58) Field of Classification Search
CPC ...... A61M 1/0281; A61M 1/34; A61M 1/362; A61M 1/3679; A61M 2202/09; A61M 2205/3334; A61M 1/3472; A61M 1/3475; A61M 1/38; B01D 63/02; B01D 63/16; B01D 61/243; B01D 61/28; B01D 2315/04
See application file for complete search history.

(56) References Cited

U.S. PATENT DOCUMENTS

| | | | | |
|---|---|---|---|---|
| 5,211,850 A | * | 5/1993 | Shettigar | A61M 1/3472 210/195.2 |
| 5,858,238 A | * | 1/1999 | McRea | A61M 1/3472 210/252 |

(Continued)

*Primary Examiner* — John Kim
(74) *Attorney, Agent, or Firm* — Riverside Law LLP (57) ABSTRACT

A method for filtering blood is disclosed that in one embodiment includes the steps of depositing unfiltered blood along at least one side of a semi-permeable surface having multiple pores, depositing target tissue along at least an opposing side of the semi-permeable surface, and permitting the unfiltered blood to flow at least partially along the semi-permeable surface to filter the unfiltered blood. Embodiments of the invention can remove self-directed autoantibodies from the blood while reducing the complications of conventional treatments such as plasmaphoresis, and return the patient's own blood cells and its plasma components, less the disease-causing self-directed antibodies. A blood filter and a blood bag are also disclosed.

12 Claims, 8 Drawing Sheets

(51) Int. Cl.
*B01D 61/28* (2006.01)
*A61M 1/38* (2006.01)
*B01D 61/24* (2006.01)

(56) References Cited

U.S. PATENT DOCUMENTS

| | | | | |
|---|---|---|---|---|
| 6,099,730 | A * | 8/2000 | Ameer | A61M 1/16 210/321.67 |
| 6,528,057 | B1 * | 3/2003 | Ambrus | A61K 35/14 210/645 |
| 2002/0182188 | A1 * | 12/2002 | Reid | C12N 5/0672 424/93.21 |
| 2005/0006296 | A1 * | 1/2005 | Sullivan | A61M 1/1696 210/321.6 |
| 2013/0112620 | A1 * | 5/2013 | Mueller | A61M 1/26 210/646 |

* cited by examiner

ANTIGENIC DECOY ENTRAPMENT FILTRATION DEVICE AND TREATMENT METHODS FOR AUTOIMMUNE DISORDERS

CROSS-REFERENCE TO RELATED APPLICATIONS

This application claims priority to U.S. provisional application No. 62/411,732 filed on Oct. 24, 2016 incorporated herein by reference in its entirety.

BACKGROUND OF THE INVENTION

Autoimmune disorders afflict many patients spanning all age groups, and often result in lifetime disabilities, if not death. Conventional management of autoimmune disorders requires anti-inflammatory medications for mild cases, and immunosuppressive treatment for moderate and severe cases. Arthritis, colitis, multiple sclerosis, vasculitis, nephritis, lupus, scleroderma, type 1 diabetes, and pemphigus vulgaris (PV) are just a few examples of the types of disorders that require long term immunotherapy, immunosuppression, and anti-inflammatory treatments. Complications associated with these treatments are well documented, and may include for example fever, vomiting, chills, nausea, aches, loss of appetite, fatigue, trembling and increased risk for disease.

Plasmapheresis is one particular type of treatment that is widely used to treat autoimmune disorders by removing antibodies. Normally, the antibodies in a patient's blood protect the patient's body from foreign objects, such as viruses and bacteria. However, in the case of autoimmune disorders, antibodies may mistake the patient's own cells as a foreign object and attack them. Generally, plasmapheresis is an extracorporeal therapy that involves passing the patient's blood though a machine that filters and separates plasma components, and treats or replaces these components before returning the blood to the patient, effectively removing antibodies. Exemplary blood filter designs are disclosed for example in U.S. Pat. No. 4,201,673 to Kanno et al., U.S. Patent Publication No. 2006/0243653 to Heinrich et al., U.S. Patent Publication No. 2014/0263018 to Fuhriman and U.S. Patent Publication No. 2013/0112620 to Mueller. While plasmaphoresis has known benefits in the acute phase of autoimmune attack, it is associated with complications from removal of plasma and replacing it with saline or Ringers solution. Further, plasmaphoresis is often associated with autoimmune rebound, which occurs when the body rapidly replaces the lowered immunoglobulin content of the blood.

It is understood that in autoimmune disorders, there are circulating antibodies that are auto- or self-reactive, as they specifically bind to molecules present on the patient's own cells and direct immune reactions against those cells. In a disorder like arthritis, the immunological response attacks tissues in the joints. In colitis, it is thought that the immunological response attacks the colon, and creates an inflammatory disorder of the large intestine. In autoimmune thrombocytopenia, it is believed that the immune system attacks the platelets. In many autoimmune disorders, it is the immunoglobulin that attaches to the surface of the target cell, and triggers an inflammatory cascade, which is a sequence of metabolic events mediated by other cells. Then, immunologically tagged cells are recognized by the immune system as apparently foreign, although they are not. In this way, the hallmark of autoimmune disorders is that the immune system mistakenly identifies "self antigens" on "self cells" as foreign material, and thereby mounts a destructive inflammatory process. Thus, while plasmaphoresis therapy is known to be effective at removing antibodies, regardless of their binding specificities, it would be more beneficial to specifically remove sefl-reactive antibodies, thereby reducing complications of plasmaphoresis resulting from removing antibodies indiscriminately, thereby maximizing patient comfort and outcomes, preserving the patient's ability to mount antibody-mediated immune responses against truly foreign materials, while minimizing the additional healthcare costs associated with treating the side effects of plasmaphoresis.

Thus, what is needed in the art is a device and method that can remove autoreactive antibodies without the complications of plasmaphoresis, and return the patient's own blood cells and plasma components, less the autoimmune disease-causing self-reactive antibodies.

SUMMARY OF THE INVENTION

A method for filtering blood includes the steps of depositing unfiltered blood along at least one side of a semi-permeable surface having multiple pores, depositing target tissue along at least an opposing side of the semi-permeable surface, and permitting the unfiltered blood to flow at least partially along the semi-permeable surface to filter the unfiltered blood. In one embodiment, the method includes the step of removing target tissue that has antigenically bonded with self-reactive antibodies from the unfiltered blood. In one embodiment, the semi-permeable surface is a wall of a hollow fiber, and wherein the unfiltered blood is deposited in a lumen of the hollow fiber. In one embodiment, the unfiltered blood is deposited in a plurality of hollow fibers, each having a semi-permeable surface having multiple pores. In one embodiment, the target tissue is a suspension of morselized target tissue. In one embodiment, the method includes the step of introducing a flow of the suspended morselized target tissue about the opposing side of the semi-permeable surface. In one embodiment, the method includes the step of introducing fresh suspended morselized target tissue about the opposing side of the semi-permeable surface and removing a used morselized target tissue away from the semi-permeable surface. In one embodiment, the semi-permeable surface is a layer of filter membrane disposed above a layer of morselized target tissue. In one embodiment, the target tissue is morselized cadaveric tissue. In one embodiment, the method includes the step of depositing the unfiltered blood by withdrawing the blood from a patient. In one embodiment, the method includes the step of removing the filtered blood away from the semi-permeable surface. In one embodiment, the method includes the step of returning the filtered blood back to the patient. In one embodiment, the method includes the step of applying a vibratory force to the unfiltered blood during the step of permitting the unfiltered blood to flow.

In one embodiment, a blood filter includes a target tissue inlet in fluid communication with a tissue suspension chamber, a blood inlet, a blood outlet, and multiple hollow semi-porous fibers providing fluid communication between the blood inlet and outlet, where the plurality of hollow semi-porous fibers are disposed within the tissue suspension chamber, where the semi-porous fibers each have a plurality of pores configured to pass large molecules and contain blood cells, and where the tissue suspension chamber is configured to hold a suspension of target tissue introduced through the target tissue inlet. In one embodiment, the filter includes an inlet funnel providing fluid communication between the semi-porous fibers and the blood inlet, and an outlet funnel providing fluid communication between the semi-porous fibers and the blood outlet, where the inlet funnel is configured to flow unfiltered blood into lumens of the semi-porous fibers, and wherein the outlet funnel is configured to collect filtered blood from the lumens of the semi-porous fibers. In one embodiment, a vibratory driver is attached to at least one of a side surface and a bottom surface of the filter. In one embodiment, the vibratory driver is configured to vibrate at between 20 and 50 kHz. In one embodiment, the vibratory driver is configured to vibrate at between 60 and 140 beats per minute.

In one embodiment, a blood bag includes a blood inlet, a filter membrane and a layer of morselized target cadaver tissue disposed adjacent to the filter membrane.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

It is to be understood that the figures and descriptions of the present invention have been simplified to illustrate elements that are relevant for a more clear comprehension of the present invention, while eliminating, for the purpose of clarity, many other elements found in systems and methods for filtering blood and treating autoimmune disorders. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

"Antibody" as used herein refers to a polypeptide, or a fragment thereof, encoded by an immunoglobulin gene, that specifically binds to and recognizes an antigen, and includes IgG, IgM, IgA, IgD and IgE, The term "antigen" as used herein is defined as any molecule that provokes an immune response. This immune response may involve antibody production, and/or the activation of specific immunologically-competent cells, or both. The skilled artisan will understand that any macromolecule, including virtually all proteins or peptides, can serve as an antigen.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is an antigenic decoy entrapment filtration device and treatment methods for autoimmune disorders.

Embodiments of the invention can remove self-directed (a.k.a., self-specific, self-reactive, auto-reactive, misdirected, dyslexic, etc.) pathological autoantibodies from the blood while reducing the complications of conventional treatments such as plasmaphoresis, and return the patient's own blood cells and its plasma components, less the disease-causing self-directed antibodies.

Figure 1:
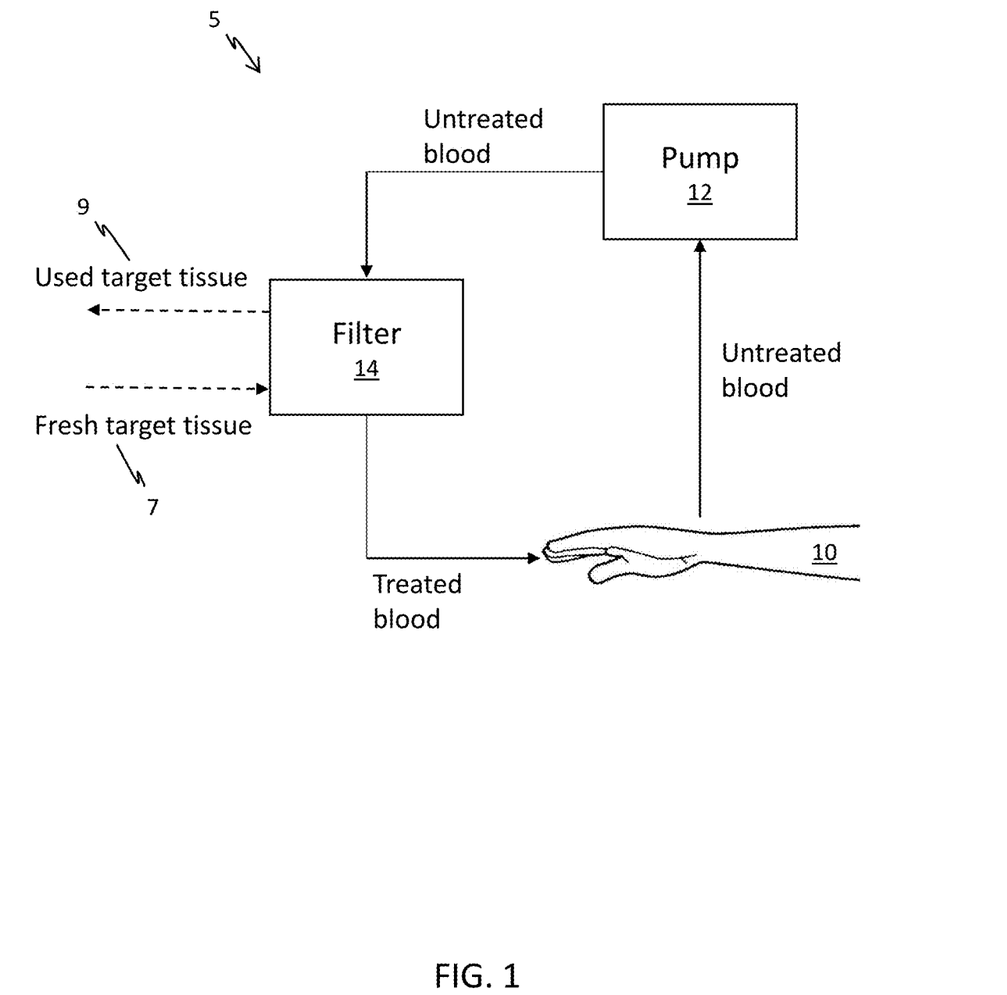
FIG. 1 is a diagram of an extracorporeal blood circuit according to one embodiment.

With reference now to FIG. 1, an extracorporeal blood circuit 5 utilizing a filter 14 according to embodiments described herein is shown. The filter 14 treats untreated blood from the patient 10 by utilizing a decoy target tissue instead of a dialysate, as used in conventional systems. In some embodiments, the decoy target tissue is a suspension of morselized decoy target tissue. In one embodiment, blood is drawn from the patient 10 utilizing a vascular access technique, such as for example venous-to-venous catheter access, or an arterial-to-venous access fistula. The blood is pumped from the patient 10 via a standard blood pump 12, and is fed to the filter 14. A decoy target tissue 7 is fed to the filter for antigenic bonding with misdirected antibodies from the patients' blood, as will be explained in further detail below. The used target tissue 9 is collected in a separate container for disposal. The treated filtered blood returns to the patient 10.

Figure 2:
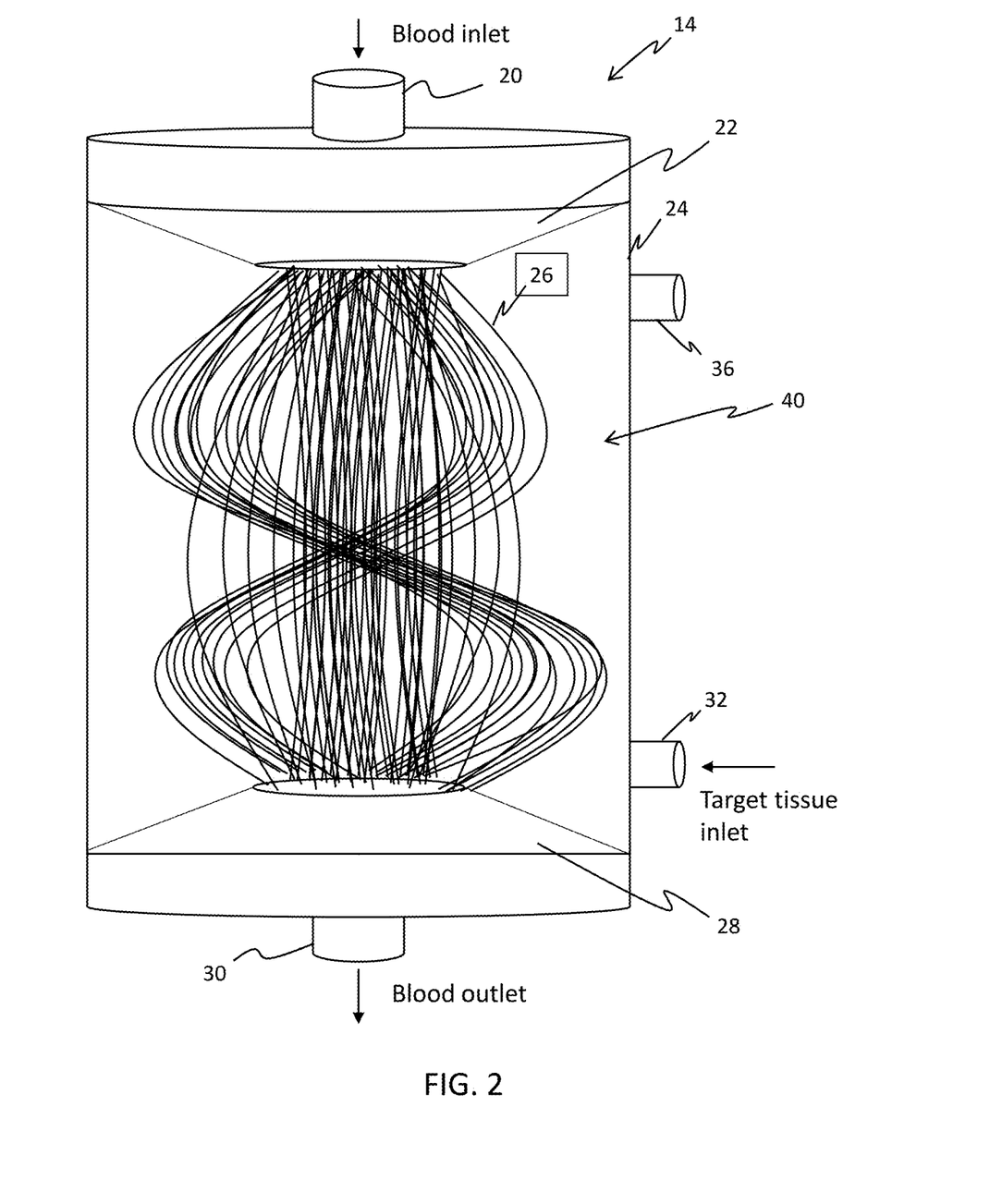
FIG. 2 is an elevated side view of a filter according to one embodiment.
Figure 3:
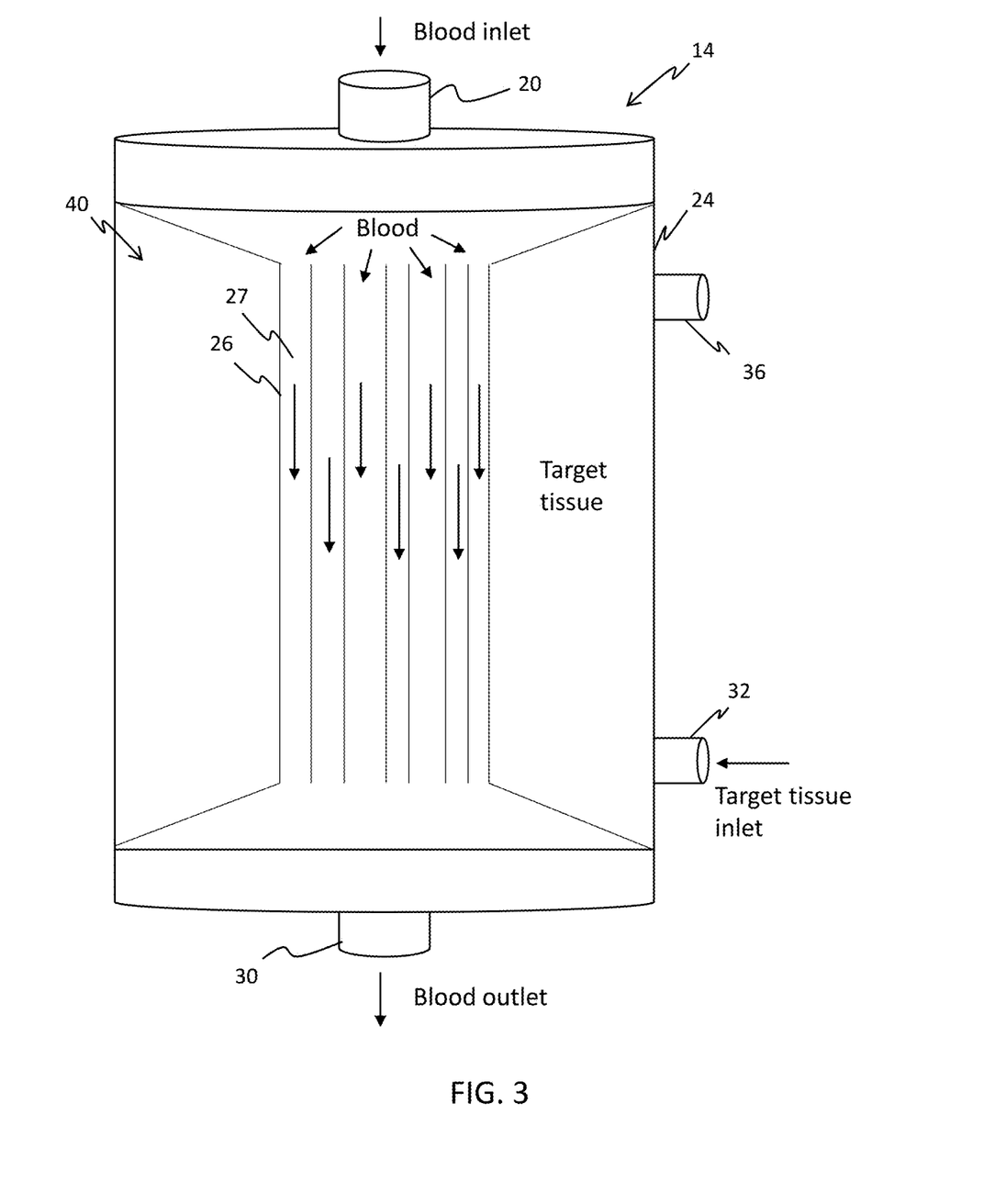
FIG. 3 is a diagram showing blood flow through a filter according to one embodiment.
Figure 4:
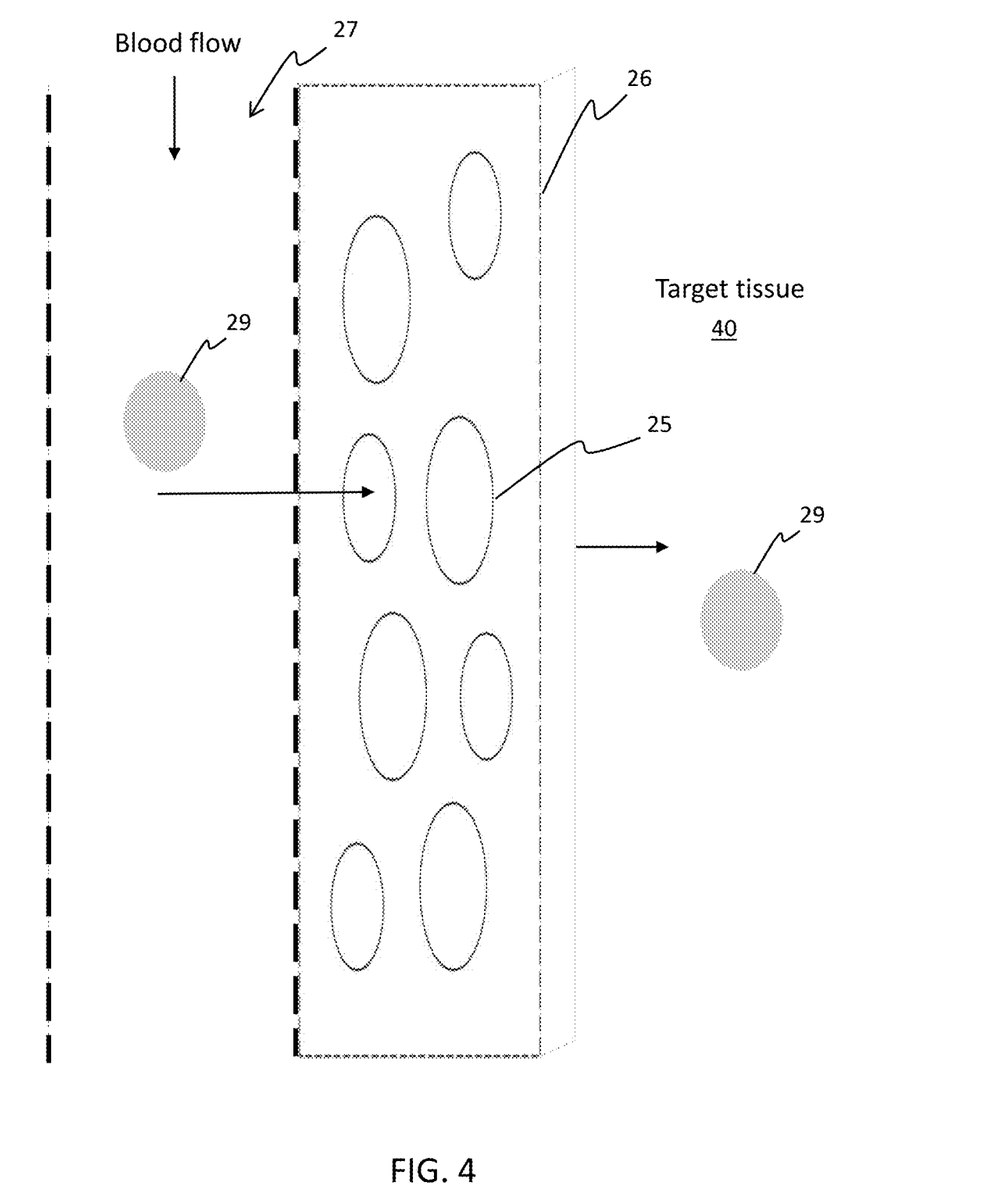
FIG. 4 is a magnified cross-sectional view of a semi-porous hollow fiber according to one embodiment.

An exemplary embodiment of a filter 14 is shown in FIG. 2. The filter 14 has a housing 24 that forms the outer wall of 
a tissue suspension chamber 40. The top of the tissue suspension chamber 40 is bounded by an inlet funnel 22 and the bottom of the suspension chamber 40 is bounded by an outlet funnel 28. The housing can be made of medical grade polymers and plastics known in the art, and the funnels 22, 28 can be made of a biocompatible material such as silastic. A target tissue inlet 32 is in fluid communication with the suspension chamber 40 and the air vent 36. The air vent 36 allows the airless fill of fresh target tissue at the time of application. The fluid inlets and outlets can include one or more check valves, limiting valves or one-way valves. In one embodiment, the air vent has a stopcock. The suspension chamber 40 can be filled with target tissue in a tilted position while the stopcock is open with the air vent pointed up. When the chamber 40 is full, the stopcock can be closed and then positioned upright.

A bundle of hollow semi-permeable fibers 26 extends between the inlet funnel 22 and the outlet funnel 28, also providing fluid communication between the inlet funnel 22 and the outlet funnel 28. The hollow semi-permeable fibers 26 each have their own inlet and outlet for fluidly communicating blood between the blood inlet 20 and the blood outlet 30. The fibers 26 can include any number of fibers needed, and may depend in part on the particular treatment being administered and the characteristics of the patient being treated. For example, the bundle of fibers 26 can include a total number of fibers in the tens, hundreds, thousands, or up to 5,000 fibers, 10,000 fibers, 15,000 fibers, 20,000 fibers or more. Each fiber can have an inner diameter of for example up to 50 microns, 100 microns, 200 microns, 500 microns or more. Pore sizes in certain embodiments are less than 0.1 microns, 1 micron, and/or between 1 and 10 microns. In certain embodiments, pores in the fibers 26 are specifically dimensioned to maintain separation between blood cells and target tissue, while allowing self-directed antibodies to pass through the pores. A potting compound can be used according to conventional blood filter manufacturing methods for securing the inlet and outlet ends of the fibers 26 to the respective funnels 22, 28.

With reference to FIGS. 3 and 4, according to one embodiment, the semi-permeable fibers 26 receive blood flow through their lumens 27, and the pores 25 allow for diffusion of large molecule antibodies 29 into the surrounding suspended target tissue 40 which is then removed from direct contact with the walls of the porous tubes 26. Specifically, in certain embodiments, large molecules antibodies 29 can be targeted and removed from circulation (FIG. 4), thus returning existing benign blood components to the patient. Thus, embodiments of devices described herein not only feature diffusion through larger pores, but they also feature the replacement of conventional dialysate with a suspension of morselized cadaveric decoy target tissue that will antigenically bond with many of the misdirected antibodies from the patients' blood. The return filtered blood that has traveled through the filter tubes has therefore been incubated by contact with the decoy target tissue.

An advantage of having larger pores size according to embodiments described herein is that many inflammatory circulating molecules such as cytokines and interleukins will be deployed within the decoy target tissue and attack the bonded antibodies. This secondary process provides for an additional advantage to the technology, as those circulating inflammatory mediators are deployed within the disposable canister and effectively removed from circulation. Removal of such circulatory inflammatory mediators becomes a secondary advantage of the filter embodiments described herein, as fewer of such inflammatory mediators are now available to damage cells of the patient who is under autoimmune attack.

The decoy target tissue 40 can be any tissue that has the antigen to which the self-directed antibodies specifically bind. The decoy target tissue 40 can be from any source, including from a living donor, from a deceased donor, or, in some embodiments, from the patient. The decoy target tissue 40 in certain, but not all, embodiments is sourced from a cadaver and cleared for tissue implantation by regulatory agencies. The tissue can for example be similar to that provided by AlloSource (Centennial, Colo.), which supplies worldwide medical centers with cadaver based tissues for variety of surgical implantations. Although the higher standard of tissue implantation is reached by the tissues used in the application of embodiments described herein, the tissue is used as an entrapment filter and is then discarded. Embodiments described herein do not rely on the tissue for permanent implantation, as it is primarily used for contact filtration of blood. Certain embodiments include secondary cultured tissue samples or sources. In some embodiments, the decoy target tissue 40 is suspension of morselized decoy target tissue. In some embodiments, the decoy target tissue 40 is suspension of morselized cadaveric decoy target tissue. The skilled artisan will understand that any cell or tissue, in whole or in part, or combination of cells or tissues or components thereof, can be used as the decoy target tissue of the invention, so long as the cell(s) or tissue(s), in whole or in part, contains the antigen to which the self-reactive antibody specifically binds. Examples of tissues useful in the devices and methods of the invention include, but are not limited connective tissues (including fibrous connective tissues, skeletal connective tissues, and fluid connective tissues, blood, bone, tendon, ligament, adipose and areolar tissues, etc.), muscle tissues (including visceral or smooth muscle, skeletal muscle, and cardiac muscle, etc.), nervous or neural tissues (including from the central nervous system (brain, spinal cord, etc.), the peripheral nervous system (cranial nerves, spinal nerves, motor neurons, etc.), epithelial tissues (including skin, the airways, reproductive tract, digestive tract, simple squamous epithelium, stratified squamous epithelium, simple cuboidal epithelium, transitional epithelium, pseudostratified columnar epithelium, columnar epithelium, glandular epithelium, ciliated columnar epithelium, etc.), endothelial tissues (blood vessels, lymph vessels, etc.) and any combination thereof, as well as any cell or any component thereof.

For specific autoimmune disorders, the decoy target tissue will be specifically selected. For example, in the case of PV, the molecular antigenic target is desmoglein 1,3. A dermatome is selected to harvest dermal skin rich in desmoglein 1,3, present on the surface of keratinizing cells. In some embodiments, the dermatome specimen is perforated and mechanically morselized to increase the surface area of target tissue to facilitate antigenic bonding to exposed keratinizing cells on skin surface. This specimen can then be washed to remove small free tissue particles, and encased in porous internal bag. Other tissues can be used in other autoimmune disorders that offer entrapping antigens to the self-directed antibodies of the specific patient undergoing antigenic decoy entrapment filtration treatment. In another example, in the case of arthritis, the decoy target tissue could be knee cartilage and/or the synovial capsule. In another example, in the case of colitis, the decoy target tissue could be the mucosa and intima of the colon. In another example, in the case of Diabetes Type 1, the decoy target tissue could be the pancreatic insulin-producing cells. Autoimmune diseases and disorders treatable with the devices and methods of the invention, include but are not limited to, Examples of autoimmune disease include but are not limited to, alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune parotitis, autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis, diabetes mellitus, discoid lupus, essential mixed cryoglobulinemia, dystrophic epidermolysis bullosa, epididymitis, fibromyalgia-fibromyositis, glomerulonephritis, Graves' disease, Guillain-Barre syndrome, Hashimoto's thyroiditis, hemolytic anemia, idiopathic pulmonary fibrosis, idiopathic thrombocytopenia purpura (ITP), IgA nephropathy, juvenile chronic arthritis (Still's disease), juvenile rheumatoid arthritis, Meniere's disease, mixed connective tissue disease, multiple sclerosis, myasthenia gravis, myxedema, pemphigus vulgaris, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, spondyloarthropathies, stiff-man syndrome, systemic lupus erythematosus, Takayasu arteritis, temporal arteritis/giant cell arteritis, thyroiditis, ulcerative colitis, uveitis, vasculitis, vitiligo and Wegener's granulomatosis. The skilled artisan will understand that the devices and methods of the invention described herein are useful for any autoimmune disease or disorder in which a self-reactive antibody has role in the pathological mechanism.

In one embodiment, to ensure that close contact with decoy target tissue does not induce other nonspecific decoy target-reactive antibodies and inflammatory response, the decoy target can first be morselized to increase antigenic surface area, then washed with ringers lactate or Normal saline to remove tissue particles that are smaller than 5 micron pores in our filtration membrane. This will prevent such particles from reentering circulation by virtue of back diffusion. Since the same membrane prevents blood cell contact with decoy target tissue, the host graft response is blocked even in cadaver tissue already cleared for more permanent implantation.

Amplification features can be implemented according to certain embodiments. For relatively small molecules and more so for larger molecules, the diffusion process, normally dependent in principle on thermal Brownian movement, can be enhanced or amplified by several mechanisms. Lateral movement via curved or spiraled fibers (e.g. FIGS. 2 and 5B) and osmotic pressure can be implemented in the filter as known in the art. With reference now to the filter 114 and vibratory elements 150, 160 shown in FIGS. 5A and 5B, in one embodiment, a vibratory mechanism 150 is implemented that will not only extend micro circulatory eddy currents, but will impart greater efficiency to the diffusion process between the blood within the porous tube and the surrounding "tissue dialysate". In one embodiment, the sides of the tissue suspension chamber 40 will be clamped down by two opposing piezoelectric elements capable of delivering 120 watts of ultrasonic agitating energy to help diffused immunoglobulins to bind to target decoy tissue. In one embodiment, the desired frequency range is be 20-50 khz. It will also enhance the antibody binding to the decoy target tissue antigen within the dialysate matrix. This vibratory driver can be electromechanical, and in certain embodiments is a piezoelectric crystal firmly attached to the outside of the filter canister. In one embodiment, the vibratory mechanism is configured to vibrate at between 40 and 40 kHz. The vibratory driver is configured to be able to impart vibratory energy to the contents of the canister during active filtration and antigenic bonding with decoy tissue.

Figure 5A:
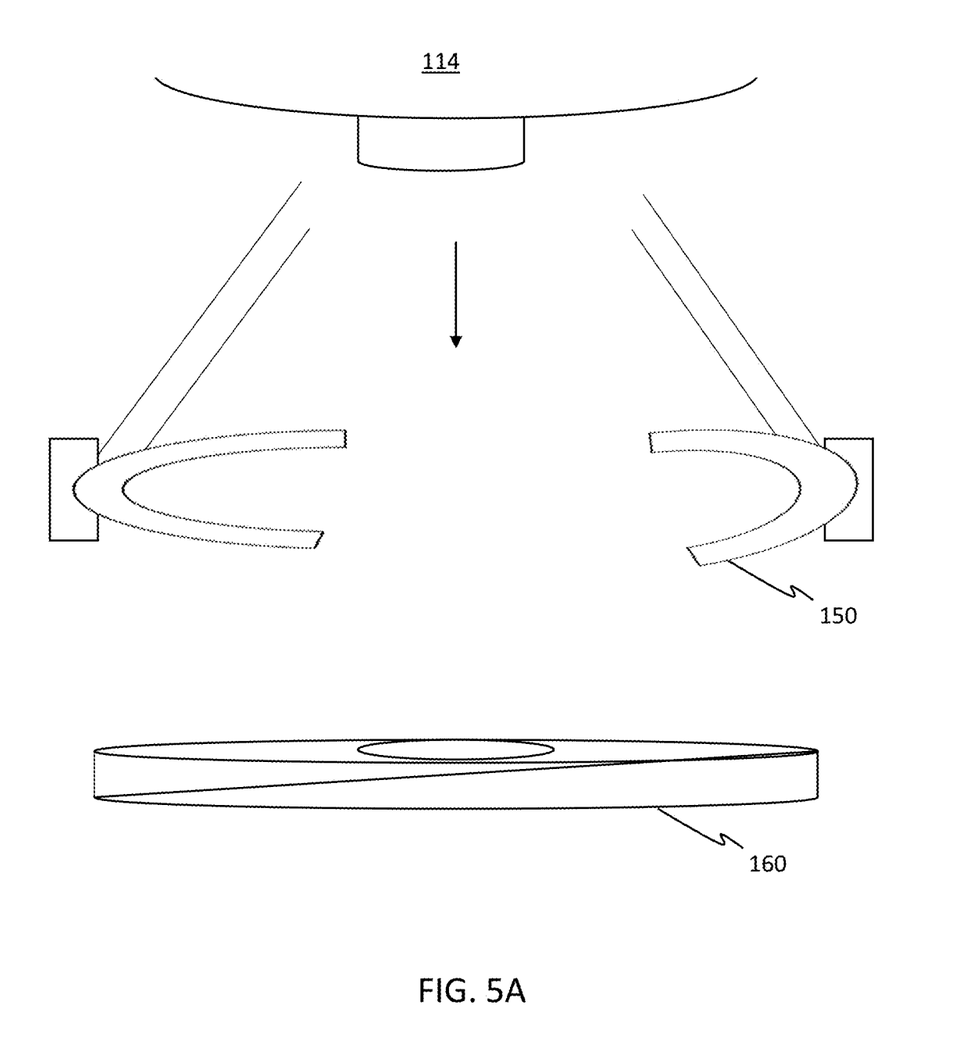
FIG. 5A is a diagram of a clamp and platform mounting system having integrated vibratory mechanisms according to one embodiment.
Figure 5B:
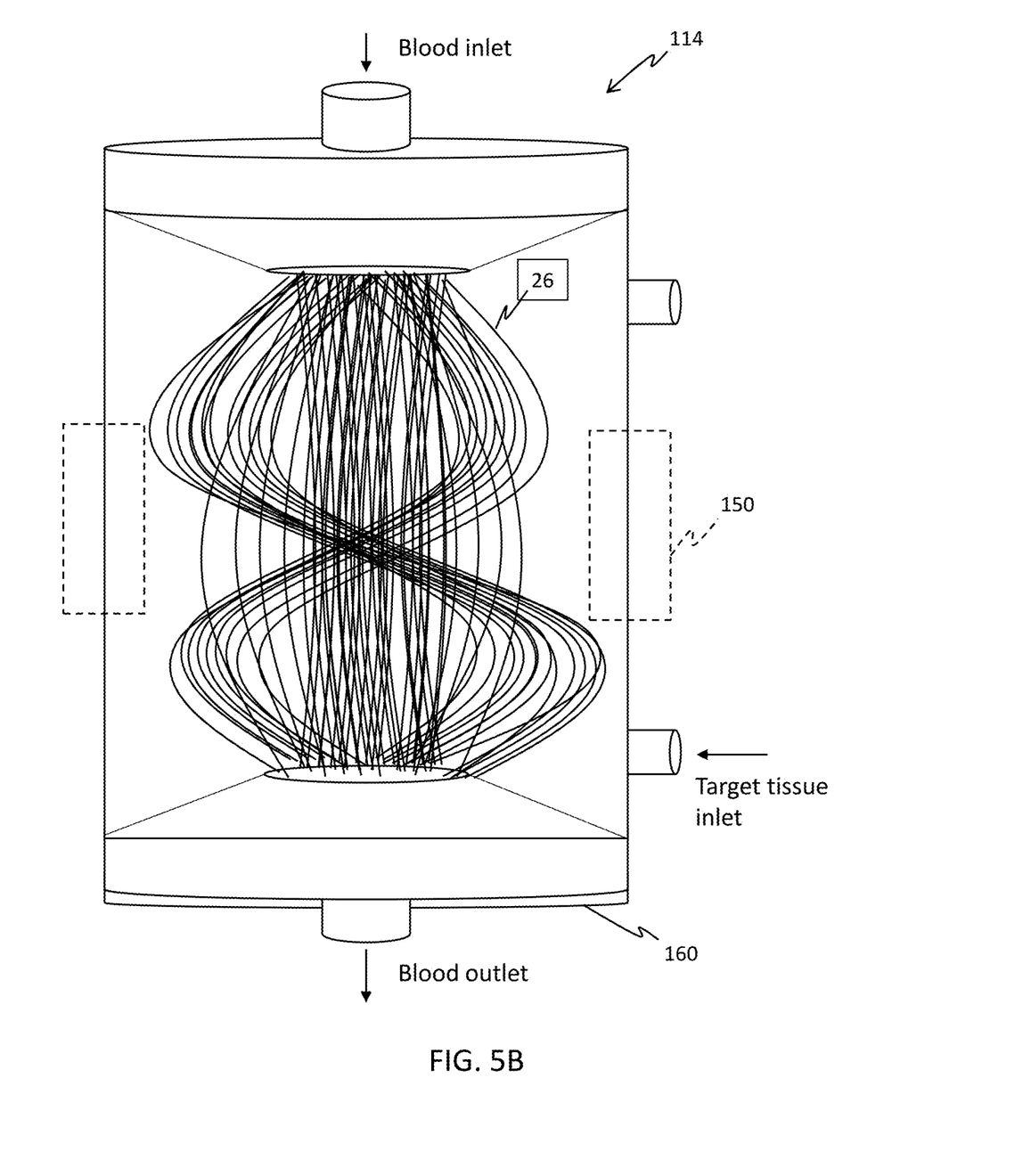
FIG. 5B is an elevated side view of a filter having vibratory amplification features according to one embodiment.

The filter can rest onto a vibratory platform 160 attached to the bottom of the filter 114. In one embodiment, the vibratory platform is configured to vibrate at between 30 and 200 Hz. The vibratory platform 160 in certain embodiments will be subject to low frequency vibrational motion in range of 60-140 beats per minute that will help at the porous tube with diffusion of the immunoglobulins into the surrounding tissue decoy target. In addition, this vibration (which may actually be coupled to the peristaltic pump) will help blood flow through the tubular elements by virtue of simulating the pulsatile nature of actual blood flow. For millions of years of evolution blood gives up its delivery nutriments and immunoglobulins to the surrounding tissues in a flow pulsatile environment. The low frequency vibration applied to the whole canister improves the immunoglobulin diffusion and red and white cells are retained within the lumen of the internal tubes. It is the motion of the tubes within the canister that amplifies the diffusion effect.

In certain embodiments, at the end of the filtration procedure, the canister filter with tubes and decoy tissue are disposed. The external ultrasonic and vibrational platforms are within the unit that houses the filter cartridge and will function to retain the next treatment cartridge. The connecting blood flow tubing is also disposable.

In some embodiments, the energy levels of vibrational mechanisms are limited so as not to cause damage to any of the blood components. The frequency of vibratory amplification can be manipulated based on the canister, and several frequencies may be used where one is optimal for enhanced tubular flow and the other for optimal antigenic admixture and bonding between self-directed antibodies in the blood and exposed antigens of the decoy target tissue used for entrapment of such self-directed antibodies. The attachment of vibratory mechanism to embodiments of the filtration enhances the efficiency of the process of removing autoimmune antibodies from circulation.

Embodiments of the invention can be implemented in a less complex blood bag filtration mechanism. Blood collection centers typically require less clinical complexity than dialysis centers, and treatment of autoimmune disorders does not require such intense intervention. A blood bag configuration may also serve as a maintenance modality for those patients who no longer require intense intervention as described in previous embodiments. In conventional systems, such as the Hemosep by Advancis Surgical (Nottingham, UK), a blood bag includes a filter membrane layer and a super absorbent pad layer. The filter membrane layer has a pore structure size and geometry designed to control what is able to pass through during filtration, so that no cellular components can pass onto the super absorbent pad. The super absorbent pad absorbs unwanted blood products that passed through the filter membrane, holding them for disposal. The following embodiment utilizes a decoy target tissue, such as a morselized cadaveric decoy target tissue, instead of the super absorbent pad.

Figure 6:
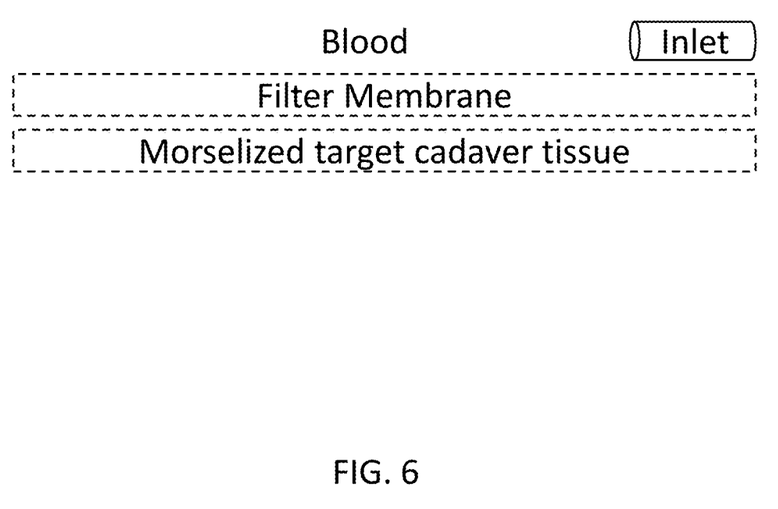
FIG. 6 is a diagram of the elements inside a blood bag according to one embodiment.

With reference now to FIG. 6, a blood bag according to one embodiment includes a filter membrane layer and a morselized target cadaver tissue layer, which is intended to bind the circulating pathological autoantibodies. Such targeted entrapment will allow autoantibody depleted blood to be returned to the patient. Similar to the previous embodiments described above, the blood bag can be in direct contact with a vibratory electromechanical source which would accelerate the antigenic binding to the decoy target tissue and substantially shorten the necessary contact incubation period leading to significant decrease of the circulating pathological autoantibodies. The arrangement of the filter membrane layer relative to the morselized target cadaver tissue layer can change depending on the application. Although this example employs, morselized target cadaveric tissue, the skilled artisan will understanding that non-cadaveric and/or non-moreslized decoy tissue could also be employed.

Figure 7:
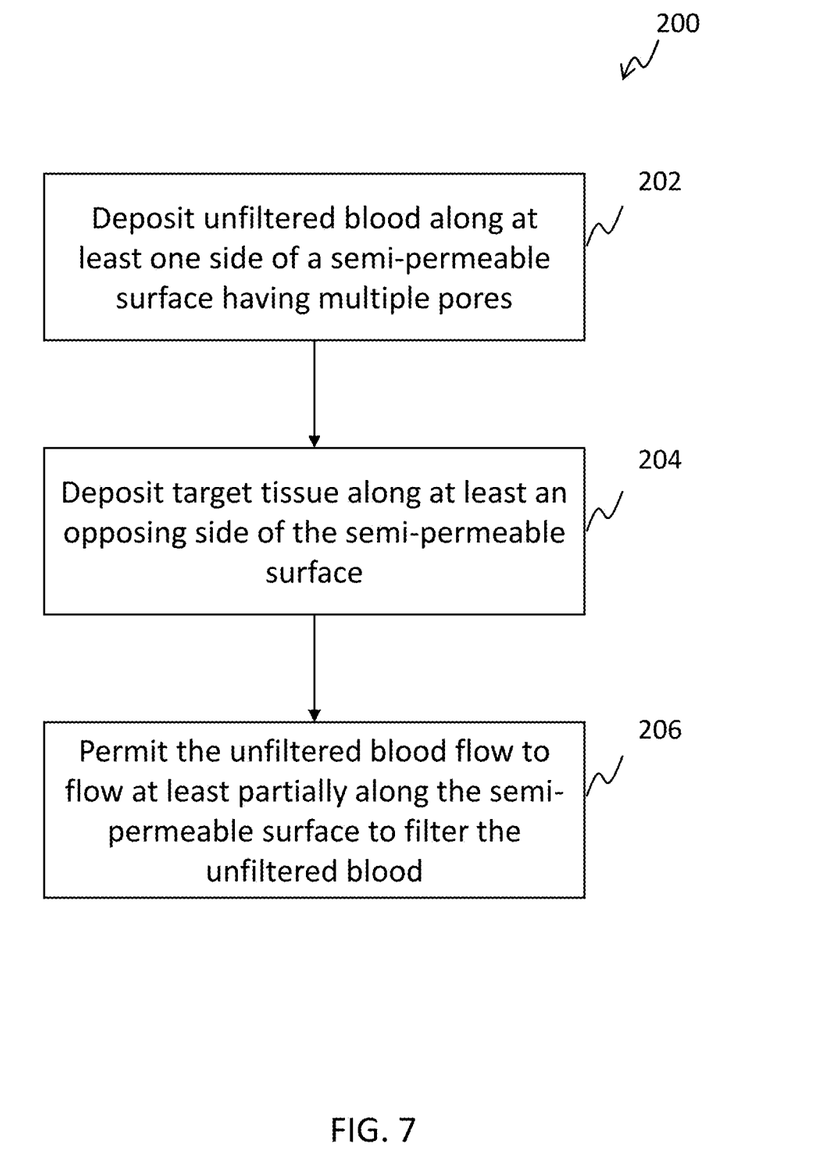
FIG. 7 is a flow chart of a method for filtering blood according to one embodiment.

With reference now to FIG. 7, a method for filtering blood is described according to one embodiment. In one embodiment, the method 200 includes the steps of depositing unfiltered blood along at least one side of a semi-permeable surface having multiple pores 202, depositing target tissue along at least an opposing side of the semi-permeable surface 204, and permitting the unfiltered blood to flow at least partially along the semi-permeable surface to filter the unfiltered blood 206. In one embodiment, the target tissue that has antigenically bonded with self-directed antibodies from the unfiltered blood is removed from the system. In one embodiment, the semi-permeable surface is the wall of a hollow fiber, and the unfiltered blood is deposited in a lumen of the hollow fiber. In one embodiment, the unfiltered blood is deposited in multiple hollow fibers, each having a semi-permeable surface having multiple pores. In one embodiment, the target tissue is a suspension of morselized decoy target tissue. In one embodiment, suspended morselized target tissue is positioned at the opposing side of the semi-permeable surface. In one embodiment, fresh suspended morselized target tissue is introduced about the opposing side of the semi-permeable surface. In one embodiment, the semi-permeable surface is a layer of filter membrane disposed above a layer of morselized target tissue. In one embodiment, the morselized target tissue is cadaveric tissue. Depositing the unfiltered blood by withdrawing the blood directly from a patient. In one embodiment, the filtered blood is removed away from the semi-permeable surface. In one embodiment, the filtered blood is returned directly back to the patient.

Advantageously, the devices and methods described herein intervene in the autoimmune attack at the point of removing at least a portion of the autoimmune antibodies circulating in the blood stream, thereby attenuating their pathological attachment to self-tissue sites. According to the embodiments described herein, the device at least partially removes self-directed antibodies that would have otherwise attached to patient tissue targets and an immune response against the patient's tissues by the patient's own immune system. Pemphigus Vulgaris, Rheumatoid arthritis, Lupus, IBD, Type I Diabetes are but a few examples of diseases that can potentially can be treated by devices and methods described herein. Embodiments described herein can be used alone or in conjunction with—before, during or after—other immunotherapy and/or immunomodulation therapies. The antigenic decoy entrapment filtration device and treatment methods can be used alone or in conjunction with—before, during or after—other pharmacological treatments. The devices and methods described herein can result in longer-term benefits and a decrease in the complications associated with traditional therapies, such as plasmaphoresis.

The following example relates specifically to treating pemphigus vulgaris to illustrate certain benefits of embodiments of the invention. Pemphigus vulgaris is an example of an autoimmune disorder that is presented by antibodies attacking on the molecules in the skin. Within pemphigus vulgaris, studies have identified desmoglein 1,3 as being the target molecule within the skin's surface that is pathologically misrecognized as an anti-desmoglein 1,3. At that point, antibodies, such as IgG antibodies, that specifically bind to desmoglein are produced and an immunological cascade is triggered. Because desmoglein 1,3 are molecules that are responsible for the adhesion of the keratin cells, the clinical presentation of pemphigus vulgaris is a blistering skin disorder. The surface cells separate from each other, and fluid-filled blisters occur, followed by open wounds that do not easily heal. In more severe cases, large surfaces of the skin are affected, and the breakdown of the skin barrier results of bacterial invasion of the system. Before the onset of immunological therapies, pemphigus vulgaris had a 80% mortality rate.

Common treatments initially involve prescribing high doses of systemic steroids, which suppresses the immunological response, but also has serious side effects. In more recent years, specific monoclonal antibodies were used against the B cells that produced the self-reactive antibodies, such as rituximab. There is new research in progress that is designing more specific monoclonal antibodies against cells that manufacture specific desmoglein 1,3 antibodies. This indeed would be beneficial treatment if the specific target is the self-directed antibodies. Unfortunately, the current treatments involve a more generalized destruction of the immune system and create vulnerability to infections and other disorders. The other problem with current treatments is that the viability of a specific immunoglobulin is about 120 days, so while the precursor cells are being suppressed with monoclonal antibody treatment, the patient continues to be subjected to the destructive immunological attack. It should be appreciated that embodiments of the extracorporeal filtration devices and methods described herein can complement such a treatment by specifically target the misdirected antibodies and are capable of providing an immediate attenuation of the immunological attack.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A method for treating an autoimmune disorder by filtering blood to remove self-directed autoantibodies comprising the steps of:

selecting a target tissue based on a type of autoimmune disorder being treated;

depositing unfiltered blood along at least one side of a semi-permeable surface having multiple pores;

depositing the target tissue along at least an opposing side of the semi-permeable surface;

permitting the unfiltered blood to flow at least partially along the semi-permeable surface to filter the unfiltered blood; and removing the target tissue to which self-directed antibodies have specifically binded to filter the blood.

2. The method of claim 1, wherein the semi-permeable surface is a wall of a hollow fiber, and wherein the unfiltered blood is deposited in a lumen of the hollow fiber.

3. The method of claim 2, wherein the unfiltered blood is deposited in a plurality of hollow fibers, each having a semi-permeable surface having multiple pores.

4. The method of claim 1, wherein the target tissue is a suspension of morselized target tissue.

5. The method of claim 4, further comprising:
depositing the suspended morselized target tissue about the opposing side of the semi-permeable surface.

6. The method of claim 5 further comprising:
introducing fresh suspended morselized target tissue about the opposing side of the semi-permeable surface and removing a used morselized target tissue away from the semi-permeable surface.

7. The method of claim 1, wherein the semi-permeable surface is a layer of filter membrane disposed above a layer of morselized target tissue.

8. The method of claim 1, wherein the target tissue is morselized cadaveric tissue.

9. The method of claim 1 further comprising:
depositing the unfiltered blood by withdrawing the blood from a patient.

10. The method of claim 9 further comprising:
removing the filtered blood away from the semi-permeable surface.

11. The method of claim 10 further comprising:
returning the filtered blood back to the patient.

12. The method of claim 1 further comprising:
applying a vibratory force to the unfiltered blood during the step of permitting the unfiltered blood to flow.

* * * * *